US010551331B2

(12) United States Patent
Appelt et al.

(10) Patent No.: US 10,551,331 B2
(45) Date of Patent: Feb. 4, 2020

(54) MEASURING APPARATUS FOR WEAK ELECTROMAGNETIC SIGNALS FROM A SAMPLE AT LOW FREQUENCIES, IN ADDITION TO A METHOD

(71) Applicant: FORSCHUNGSZENTRUM JÜLICH GMBH, Jülich (DE)

(72) Inventors: Stephan Appelt, Aachen-Soers (DE); Martin Süfke, Aachen (DE); Bernd Alexander Liebisch, Aachen (DE)

(73) Assignee: Forschungszentrum Jülich GmbH (DE)

( * ) Notice: Subject to any disclaimer, the term of this patent is extended or adjusted under 35 U.S.C. 154(b) by 513 days.

(21) Appl. No.: 15/509,542

(22) PCT Filed: Sep. 17, 2015

(86) PCT No.: PCT/EP2015/071283
§ 371 (c)(1),
(2) Date: Aug. 24, 2017

(87) PCT Pub. No.: WO2016/042057
PCT Pub. Date: Mar. 24, 2016

(65) Prior Publication Data
US 2017/0356864 A1  Dec. 14, 2017

(30) Foreign Application Priority Data
Sep. 19, 2014 (DE) .................. 10 2014 218 873

(51) Int. Cl.
*G01N 24/08* (2006.01)
*G01N 24/10* (2006.01)
(Continued)

(52) U.S. Cl.
CPC ............. *G01N 24/08* (2013.01); *G01N 24/10* (2013.01); *G01R 33/46* (2013.01); *G01R 33/60* (2013.01)

(58) Field of Classification Search
CPC .... G01R 33/3621; G01R 33/60; G01R 33/46; G01R 33/4828; G01R 33/5611;
(Continued)

(56) References Cited

U.S. PATENT DOCUMENTS 6,150,817 A * 11/2000 Lurie ................. G01R 33/3621
324/309
2005/0116714 A1* 6/2005 Rudakov ............ G01R 33/3628
324/322
(Continued)

FOREIGN PATENT DOCUMENTS

DE        3811983 A1   10/1989
JP     2001505304 A    4/2001
JP     2007121148 A    5/2007

OTHER PUBLICATIONS

International Preliminary Report on Patentability, International Application No. PCT/EP2015/071283, dated Mar. 19, 2017, 12 pages.
(Continued)

*Primary Examiner* — Patrick Assouad
*Assistant Examiner* — Suresh K Rajaputra
(74) *Attorney, Agent, or Firm* — Barnes & Thornburg LLP (57) ABSTRACT

The invention relates to a measuring apparatus for detecting weak electromagnetic signals from a sample at low frequencies, specifically in the frequency range of 1 kHz-10 MHz, in particular, and to a measuring method. The problem addressed by the invention is that of providing an apparatus which can be used to detect weak electromagnetic signals from a sample, in particular in the frequency range of 1 kHz-40 MHz, with a good signal-to-noise ratio. For the
(Continued)

solution, the measuring apparatus comprises an electromagnetic resonant circuit having a pick-up coil of low quality, a preferably tunable capacitance and a filter coil; the filter coil and the capacitance have a high quality of at least 100, advantageously at least 200, particularly preferably at least 500. Alternatively or additionally, the quality of the resonant circuit is at least 100, advantageously at least 200, particularly preferably at least 500. The quality of the filter coil and the quality of the capacitance exceed the quality of the pick-up coil, specifically at least by twice the amount. The measurement signal is then available at the two ends of the filter coil with a good signal-to-noise ratio.

15 Claims, 4 Drawing Sheets

(51) Int. Cl.
  *G01R 33/46* (2006.01)
  *G01R 33/60* (2006.01)

(58) Field of Classification Search
  CPC .. G01R 33/565; G01R 33/3415; G01N 24/08; G01N 24/10; A61B 5/055
  See application file for complete search history.

(56) References Cited

U.S. PATENT DOCUMENTS

| | | | |
|---|---|---|---|
| 2008/0042650 A1* | 2/2008 | McDowell | G01R 33/34 324/318 |
| 2010/0090697 A1 | 4/2010 | Savukov et al. | |
| 2017/0285115 A1* | 10/2017 | Appelt | G01R 33/02 |

OTHER PUBLICATIONS

Wosik J., et al., Cryogenic varactor-tuned 4-element array and cryostat for mu-MRI of trabecular bone in the distal tibia, Proceedings of the International Society for Magnetic Resonance in Medicine, ISMRM, 16th Scientific Meeting and Exhibition, Toronto, Canada, 2008, p. 443.

* cited by examiner

MEASURING APPARATUS FOR WEAK ELECTROMAGNETIC SIGNALS FROM A SAMPLE AT LOW FREQUENCIES, IN ADDITION TO A METHOD

CROSS-REFERENCE TO RELATED APPLICATIONS

This application is the U.S. national phase of PCT/EP2015/071283, filed on Sep. 17, 2015, which claims priority to German Patent Application 102014218873.3, filed on Sep. 19, 2014. The disclosures of both German Patent Application 102014218873.3 and PCT/EP2015/071283 are hereby incorporated herein by reference in their entireties.

The invention concerns a measuring device for detecting weak electromagnetic signals from a sample at low frequencies, specifically in particular in the frequency range of 1 kHz-10 MHz as well as a measuring method.

The weak electromagnetic signal from a sample can for example originate from precession of atomic nuclei (nuclear magnetic resonance, NMR), electrons (electron spin resonance, ESR), or from oscillating magnetic nanoparticles. In such cases (nuclear spin, electron and magnetic nanoparticles), the electromagnetic signals are first of all measured with a pickup coil, which has a relatively poor quality $Q_f<30$.

In case of NMR or ESR, a sample is placed for measuring in a homogenous magnetic field $B_0$. The sample is surrounded by an excitation coil, which generates a high frequency alternating electromagnetic field vertically to the main magnetic field. A measuring device for measuring thereof resulting electromagnetic signals of the sample is known from the documents US 2008/0231277 A1, U.S. Pat. No. 7,405,567 B2 as well as U.S. Pat. No. 8,115,488 B2.

A measuring device for NMR measurement with an electromagnetic oscillating circuit with a pickup coil, a capacitance and a filter coil is known from the document WO 95/14240.

Object of the invention is the creation of a device, with which weak electromagnetic signals from a sample in particular in the frequency area of 1 kHz-40 MHz with good signal-to-noise ratio can be detected.

For solving the problem, a measuring device comprises the features of claim 1. Preferred embodiments result from the dependent claims.

The measuring device comprises an electromagnetic oscillating circuit (resonant circuit) comprising a pickup coil, a preferably tunable capacitance and a filter coil.

Capacitance and filter coil have a high quality of at least 100, preferably at least 200, particularly preferred at least 500. Alternatively or additionally, the quality of the oscillating amounts to at least 100, preferably at least 200, particularly preferred at least 500. The measurement signal is then available at the both ends of the filter coil with good signal-to-noise ratio.

The filter coil has in one embodiment a grounded center tapping in order to achieve a further improved signal-to-noise ratio.

The quality of the filter coil and the quality of the capacitance, in particular a capacitor, are generally greater than (exceed) the quality of the pickup coil, specifically preferably by many times, at least two times, particularly preferred at least by three times. The quality of the pickup coil is generally low and is preferably smaller than 30, preferably smaller than 20, particularly preferred smaller than 10. As pickup coil may serve a cylindrical inductor (coil), a surface coil or a saddle coil. The pickup coil may have only few windings, for example up to 10 windings. Wires or braids of the pickup coil and/or filter coil may consist for example of copper, silver or gold.

Preferably, the device comprises specifically in particular pickup coil and/or filter coil braids, whose thin wires are electrically insulated, specifically in particular by insulating varnish layers in order to thus arrive at a further improved signal-to-noise ratio. Existing braids are preferably high frequency resistant in order to obtain a good signal-to-noise ratio.

The following embodiments further improve alone as well as in arbitrary combination the signal-to-noise ratio:

The center tapping is located preferably exactly in the middle (center) of the filter coil. By means of the center tapping, oscillating tendencies of the oscillating circuit are suppressed, specifically very well, if the center tapping is arranged exactly centered. This positively affects the signal-to-noise ratio.

The center tapping is in one embodiment realized by an additional wire or an additional braid. One end of the additional wire or additional braid, respectively, is connected to ground (earth), i.e. grounded. Furthermore, one end of the other wire of the filter coil is connected to ground. The searched voltage, thus the searched desired signal, is then present at the remaining ends of the wires or braids, respectively. This embodiment of the coil leads to a high quality, which represents an independent invention.

For manufacturing, for example two electric conductors (in particular a first and a second wire or a first and a second braid) are twirled together, respectively twisted together. Subsequently, the both electric conductors that are twisted together are wound into a coil. The end of the first electric conductor (wire or braid) as well as the opposite end of the second electric conductor (wire or braid) are then grounded. The both other ends then form the electric terminals of the coil.

If the aforementioned both electric conductors are equally long, then the center tapping is located exactly in the middle (center).

The filter coil is shielded in particular by an electric and/or magnetic shielding. Walls of the shielding at the magnetic shielding consist preferably of Mu-metal or iron, preferably highly permeable iron.

A magnetic shielding is preferably formed by a substantially magnetically closed chamber or closed can (box).

A magnetic shielding protects advantageously from electromagnetic disturbances and thereby contributes to the improvement of the signal-to-noise ratio.

Walls of the shielding are preferably composed double-walled or within a can is located a second can, which is kept at a distance from the first can through spacers. The filter coil is then located within the second can. The shielding therefore consists particularly preferred of a double-walled chamber or double-walled can.

By means of a magnetic shielding, which is used in case of NMR or EPR, the filter coil can be magnetically shielded from a magnetic $B_0$-field in case of NMR or EPR spectroscopy. This shielding results in a further improved signal-to-noise ratio.

The walls of a double-wall of the magnetic shielding or the wall of one or two cans of the magnetic shielding are preferably 1 mm to 3 mm thick, such as for example 1.5 mm thick. Walls of an electric shielding are preferably up to 3 mm thick and/or at least 0.5 mm thick. Walls of an electric shielding are preferably slit. Walls of an electric shielding preferably consists of copper. Such a designed electric shielding contributes to a good signal-to-noise ratio.

The shielding is preferably grounded. In case of two cans, the outer can is generally grounded. But alternatively or additionally, also the inner can may be grounded.

Preferably, the pickup coil is separated from an excitation coil that is used for NMR or EPR spectroscopy. Then, also a second coil is present, which is used as excitation coil for the conduction of NMR or EPR spectroscopy. It is thereby enabled to optimize the measuring device independent from the excitation coil, which enables an improved signal-to-noise ratio. The pickup coil is located preferably inside of the excitation coil. The distance between excitation coil and pickup coil amounts to advantageously at least 5 mm, preferably at least 10 mm, in order to keeping a disadvantageously coupling between the both coils sufficiently low. The main axis of the excitation coil (=direction rf field) is arranged preferably substantially orthogonally (vertically), preferably orthogonally (vertically), to the sensitive axis of the pickup coil in order to keeping a disadvantageously coupling between the both coils sufficiently low.

Pickup coil one the one hand and capacitor as well as filter coil on the other hand are in one advantageous embodiment connected together by a particularly low-loss electric transfer line. This is achieved by a transfer line that consists of a good electric conductor, such as for example by a transfer line that consist of copper, by a large cross section of a transfer line of for example at least 1 $mm^2$, by an entwining around respectively twisting of the both electric conductors of the transfer line and/or by an appropriate electric insulation, in particular by an insulation of Teflon. Each single conductor may be placed in a Teflon casing for the purpose of insulation and/or both electric conductors of the transfer line together. A conductor may be formed of a wire or a braid.

A transfer line is preferably formed of two braids that are twisted together, which preferably comprise the aforementioned Teflon casing in order to thereby provide a particularly low-loss transfer line for EPR or NMR spectroscopy, which represents an independent invention.

If the transfer line is formed by two braids, the mentioned cross section of at least 1 $mm^2$ is related to the sum of the cross sections of the single wires of the both braids, specifically including optionally provided insulators. Braids of the transfer line are again preferably electrically insulated from each other, specifically in particular by means of painted surface coating and/or implemented high frequency resistant in order to provide a low-loss transfer line that results in a further improved signal-to-noise ratio.

The pickup coil is preferably formed by a braid, i.e. of an electric conductor consisting of thin single wires. The single wires of the braid are advantageously electrical insulated from each other. The surface of the single wires are therefore advantageously provided with an electrically insulating varnish. The braid is preferably high frequency resistant.

A toroidally or cylindrically shaped filter coil with a winding of stranded wire has proven to be appropriate. For the realization of an external resonator with high quality $Q_E>1000$, the filter coil should follow a magnetic alternating field with an energy loss as low as possible respectively have a low AC loss. For that purpose, the filter coil has to have a negligible stray magnetic field and the alternating current resistance of the winding should be as low as possible. Also other losses like for example dielectric losses or losses in magnetic core of the filter coil should be minimized.

This results in a measuring device, which acts as a bandpass filter with a relatively narrow band. Having appropriate tuning, the desired signal is let pass through. Noise signals in adjacent frequency areas are filtered out such that already for this reasons a good signal-to-noise ratio is achieved. But above all, an appropriate voltage amplification succeeds, which decisively contributes to a good signal-to-noise ratio.

Advantageously, the distance between pickup could on the one hand and capacitor as well as filter coil on the other hand amounts to at least 5 cm, preferably at least 50 cm, particularly preferred at least 60 cm. This reduces a reciprocally disturbing magnetic impact between a $B_0$ field, as this is present in case of a EPR or NMR spectroscopy, and the filter coil, which is commonly shielded. It is achieved that a shielding does not disadvantageously affect the $B_0$ field. It is further avoided that the shielding is disadvantageously saturated by the $B_0$ field.

The capacitance is advantageously tunable in order to allow adjusting a suitable resonance. Preferably, the capacitance is formed of a plurality of discrete capacitors, which are connected appropriately in parallel as well as allow connection in a way to allow changing the capacitance (capacity) as needed. Thereby, commercially available capacitors with high quality can be used in order to provide a tunable capacitance with high quality.

Advantageously, the measurement signal (i.e. the voltage being present at the filter coil) is amplified, for example first of all by a low noise pre-amplifier (preferably by a differential amplifier, particularly preferred by an instrument amplifier) and subsequently by a final amplifier (preferably by a lock-in amplifier).

The obtained signal-to-noise ratio in the abovementioned frequency range can compete with the signal-to-noise ration of the high-field NMR or EPR (400 MHz-1 GHz). The device related expenditures, which has to be spend in the abovementioned frequency range, is however advantageously considerably lower compared to high-field NMR respectively EPR. Also, the signal-to-noise ratio is only weakly dependent on the frequency, so that especially also low frequencies are possible, which enables a low technical effort. Especially, also small sample volumes are possible without considerable worsening of the signal-to-noise ratio.

It can be measured very flexibly and robustly during practical use. The entire necessary hardware allows miniaturization and allows to conduct mobile EPR or NMR spectroscopy in a frequency range of 1 kHz-40 MHz with micro coils without the use of superconductive magnets. In particular, an EPR or NMR spectroscopy at frequencies below 10 MHz and above all also below of 1 MHz can be conducted in order to allow keeping the device expenditures low. Fields of applications are the chemical analysis, the sensor technology as well as medical science.

It shows.

Figure 1:
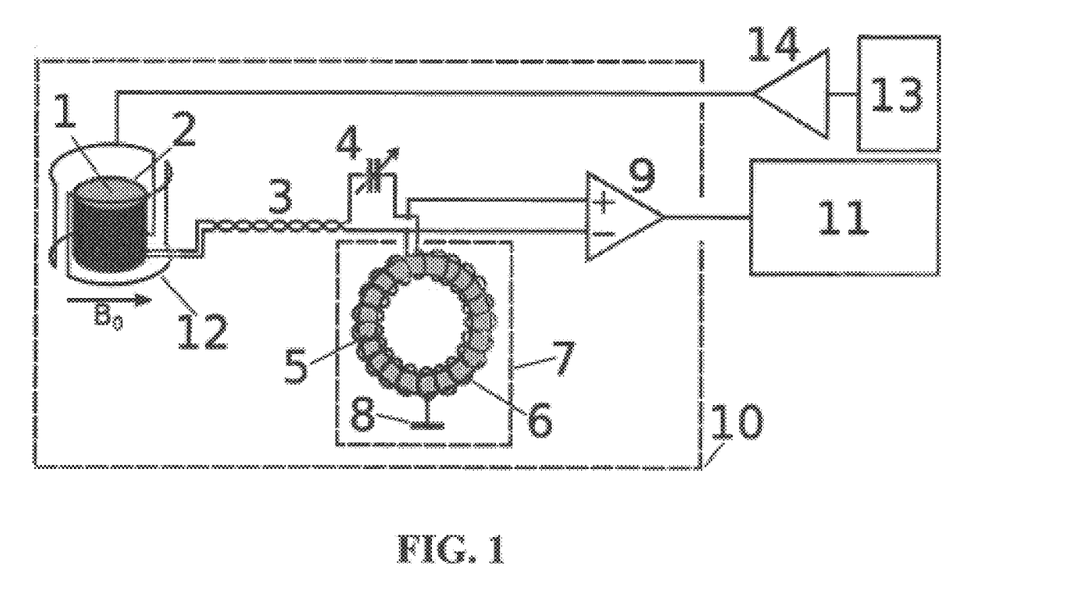
FIG. 1: Setup of an embodiment

A pickup coil 2 of any structural form that is wound around a sample 1 is connected to an external high-quality filter coil 6 through a low-loss transfer line 3 and an tunable capacitance (capacitor) 4 of high quality ($Q_c\sim10000$). The transfer line comprises two electric conductors, which each consist either of a multi-wired copper line with large cross section (>1 mm$^2$) and minimal capacity dielectrical loss due to a Teflon insulation or of thick low-resistance stranded wire (1000×0.05 mm) with negligible skin and proximity effect at frequencies below 1 MHz. The both conductors are wound around one another as shown, thus twirled or twisted together, respectively. In case of a Teflon insulation, every conductor is encased by Teflon. Additionally, the both conductors of the transfer line 3 that are twisted together are located in a Teflon casing.

The oscillating NMR signal that is recorded by the pickup coil (so called free induction decay, FID) is conducted via the transfer line 3 with low loss to the filter coil 6 with or without core 5. Due to the high quality $Q_E$ of the filter coil, the NMR signal is compared to the noise by the reducing factor $Q_{red}=Q_E/(1+R_f/R_E) \gg 100$ inflated with $R_f$=alternating current resistance of the pickup coil and $R_E$=alternating current resistance of the filter coil. The alternating voltage at the filter coil is conducted through two electric conducting connections into the inverting and non-inverting entrance of a differential amplifier 9 and further amplified there. In order to suppress the oscillating tendency of the very sensitive resonator in conjunction with the differential amplifier 9, a grounded center tapping 8 at the filter coil 6 is provided. Furthermore, the center tapping 8 provides for the draining of the technically unavoidable bias currents of the differential amplifier 9.

The filter coil 6 is separately magnetically shielded by means of a shielding 7.

Possible embodiments of filter coils with a quality $Q_E \gg 100$ are for example specially wound low-loss ferrite cores, toroidally or cylindrically shaped coils with winding of stranded wire.

Especially during the use of ferrites, the shielding 7 consists of a simple or several fold Mu-metal shielding, which shields any DC and/or AC magnetic fields. On the other hand, the for her part heavy magnetic Mu-metal shielding should not affect the homogeneity of the $B_0$ field. This is achieved by a sufficiently large distance between sample 1 and the Mu-metal shielding 7. The transfer line 3 is therefore at least ca. 10-50 cm long.

For toroidally or cylindrically shaped filter coils 6 without magnetic core 5, an electric shielding 7 is used for example made of copper sheet in order to shield electromagnetic disturbances in the frequency range of interest. The shielding 7 consists in this case in one advantageous embodiment of among each other electric insulated segments of copper and is advantageously composed such that eddy currents are avoided, which could reduce the $Q_E$. Eddy currents are avoided in particular by appropriate arranged slits.

At a cylindrically shaped filter coil 6 without magnetic core 6, the critical eddy current would for example be a circular current about the cylindrical axis of the filter coil 6, which considerably reduces the inner magnetic field of the filer coil 6. These circular currents cannot flow, if the cylindrically shaped Cu shielding, which includes the filter coil 6, consists of two halves, which do not electrically touch each other along the shell of the cylinder. Further slits of the shielding 7 in order to suppress further circular currents on the surface of the shielding cylinder are advantageously provided in the sense of an improved quality Q.

For the purpose of optimizing the signal-to-noise ratio, the differential amplifier 9 is advantageously configured such that in the considered frequency range, the current and voltage noise ($i_n$, $e_n$) is lower than the Johnson noise (background) of the input circuit. The amplified NMR signal can be either directly digitally sampled via a fast A/D converter or analogously further processed via a lock-in amplifier 11 and analyzed via a computer. The analysis system can be equipped with a bandpass filter for the purpose of improvement of the signal-to-noise ratio.

Depending on the application and the environmental conditions, the pickup coil 2 can be a cylindrical inductor (coil), a saddle coil or a surface coil with dimensions of 0.01-10 cm. The quality and shape of the pickup coil 2 does thereby play only a minor role for the signal-to-noise ratio. This is one of the big advantages of the present invention, which allows to choosing the shape and design of the pickup coil 2 entirely freely. This is important for the feasibility of NMR examination under difficult conditions. The sample 1 with the nuclear spins is located inside or on the surface of the respective pickup coil 2, depending on whether it is a cylindrical inductor (coil), a saddle coil or a surface coil.

An excitation of the nuclear spin occurs by means of a larger saddle coil 12 in conjunction with a pulsed high frequency generator 13 and a high frequency amplifier 14. On the one hand, the saddle coil 12 is far enough (~1 cm) away from the pickup coil 2 for the purpose of minimal coupling, and on the other hand, the main axis of the saddle coils (=direction rf field) is arranged orthogonally to the sensitive axis of the pickup coil 2.

The excitation of the sample 1 with a magnetic alternating field from the saddle coil 12 is practically entirely decoupled from the entire reception circuit. Therefore, the reception circuit does not require any more to be tuned to a specific impedance and can be optimized to a best possible signal-to-noise ratio independent from the transmission coil. The sample 1 is located in the homogenous magnetic field area $B_0$ of a not shown electromagnet or Hallbach magnet, which can generate a typical field strength in the range of $B_0=10^{-4}$ T–1 T. This field range corresponds for protons to a range of the Larmor frequency of f=4 kHz-42 MHz. The components 1 to 9 are electrically two-fold shielded by means of two copper and/or aluminum shields 10 that are nested into each other.

In the embodiment shown in FIG. 1, the transmission circuit is decoupled from the reception circuit. The reception circuit is physically separated (spaced apart) in an area of the signal pickup (pickup coil 2 with sample 1) and an external resonator of high quality. The decoupling of the transmission from the reception circuit allows to optimize the reception circuit separately without consideration of an impedance adaptation between transmission and reception circuit. In particular, the reception circuit can advantageously have for example several MOhm impedance, which is in particular the case at parallel resonance circuits with very high quality. Due to the second condition, the pickup coil can be freely designed independent from all other elements and does not need to have high quality. The external resonator can be optimized for highest quality and therefore for maximal amplification of the NMR signal.

Figure 2:
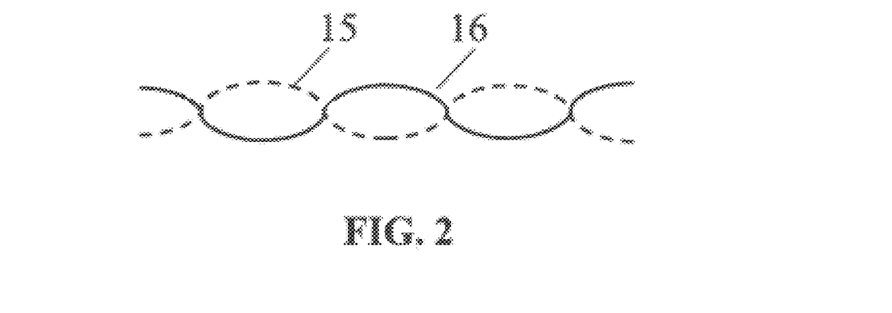
FIG. 2: Electric conductors that are twisted together for a filter coil

In the FIG. 2, two electric conductors 15 and 16 that are twisted together are shown, as they can be used for the transfer line 3 or for the filter coil 6. In case of filter coil 6, the wires 15 and 16 that are twisted together are wound into the coil. One end of the one electric conductor 15, such as for example the in the FIG. 2 left shown end, and the opposite end of the other conductor 16, thus then the right shown end, are electrically connected together and thereby form the center tapping 8, which is grounded. The remaining ends of the electric conductors 15 and 16 are then connected on the one hand with the preferably tunable capacitor 4 and on the other hand with an electric conductor of the transfer line 3.

A filter coil 6 with ferrite core 5 has the big advantage that it is relatively small and low-priced and qualities up to $Q_E \sim 500$ are realizable. Ferrite cores are commercially available in different sizes and structural shapes, for example as toroid or in closed shapes (Pot circle; coaxial cavity resonator) in order to keep the magnetic stray losses as low as possible.

Figure 3:
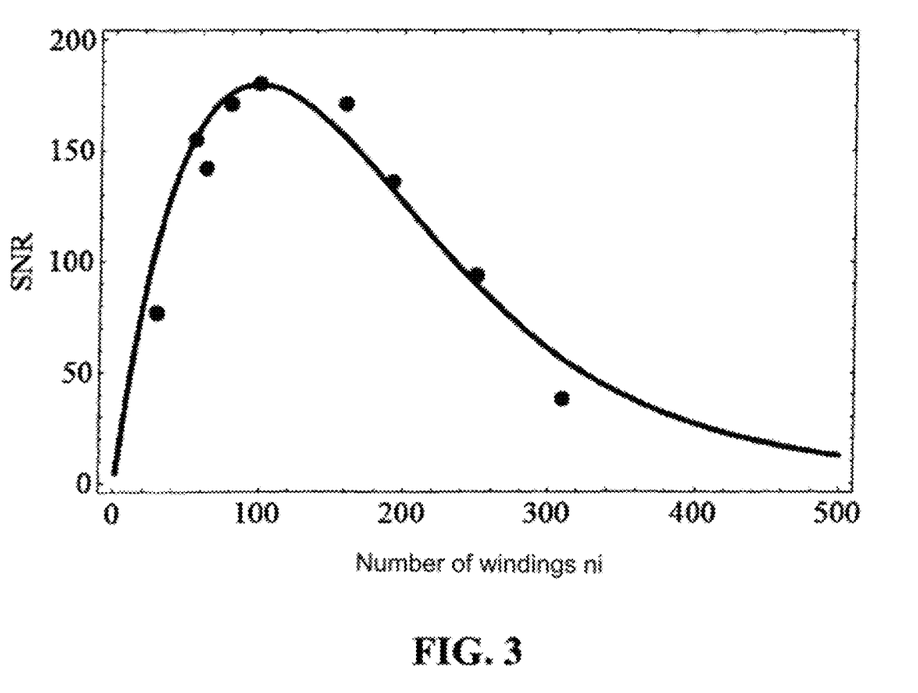
FIG. 3: Signal-to-noise ratio of 0.5 $cm^3$ benzene as a function of the number of windings nl of the pickup coil respectively input coil

Two interwoven copper wires of equal length are in one embodiment wound with few windings around the ferrite core, wherein the number of windings $n_E$ depends on the detection frequency, typically of $n_E=8$ at 8 to 500 kHz up to $n_E=104$ at 20 kHz. The intertwined winding pair of multi-wired copper or braid wire minimizes skin and proximity effect and the therewith connected AC resistance considerably. A center tapping 8 is led out exactly in the middle between both interwoven winding halves. This avoids a possible oscillating tendency of the high-quality overall circuit during grounding. All filter coils with ferrite cores react extremely sensitive to external magnetic and electromagnetic fields and are therefore preferably shielded with a magnetic two-fold shielding made of Mu-metal (shielding factor~1000). Because the both Mu-metal shields are also electric conductive, they shield besides from magnetic fields also from electromagnetic alternating fields. Different filter coils with ferrite cores were manufactured at five different frequencies with the following qualities: $Q_E=218$ at 500 kHz, $Q_E=380$ at 166 kHz, $Q_E=369$ at 83 kHz, $Q_E=280$ at 41 kHz and $Q_E=255$ at 20 kHz. The AC-resistance, the inductance, capacitance respectively the quality of all filter coils as well as all relevant components such as transfer line and tuning capacitors were measured with an impedance spectrometer as a function of the frequency and optimized. Protons ($^1$H) experiments with all five ferrites were conducted with a pre-polarized benzene (benzol) sample ($V_S \sim 0.3$ cm$^3$, $N_S=2 \times 10^{22}$ protons, $P_n \sim 1.5 \times 10^{-6}$). The pickup coil 2 was characterized by the parameter $D_i=H_c=1$ cm, $W_f=63$, $d_{Cu}=0.12$ mm, and by their overall winding number $n_f$. The measured signal-to-noise ratio (SNR) as a function of $n_f$ for the filter coil with ferrite at 500 kHz is shown in FIG. 3. The measurement points (black circles) are in good agreement with the theoretic expectation (continuous line). The parameters for the ferrite core at 500 kHz are: $L_E=116$ µH, $R_f=1.77$ Ohm and $Q_E=218$. FIG. 3 clearly shows the initially linear increase of the signal-to-noise ratio with $n_f$, then a maximum at $n_f^{max} \sim 90\text{-}100$ with signal-to-noise ratio=170, and finally the hyperbolic decrease, which is in agreement with a dominating skin effect and very weak proximity effect (~3% of skin effect).

Figure 4:
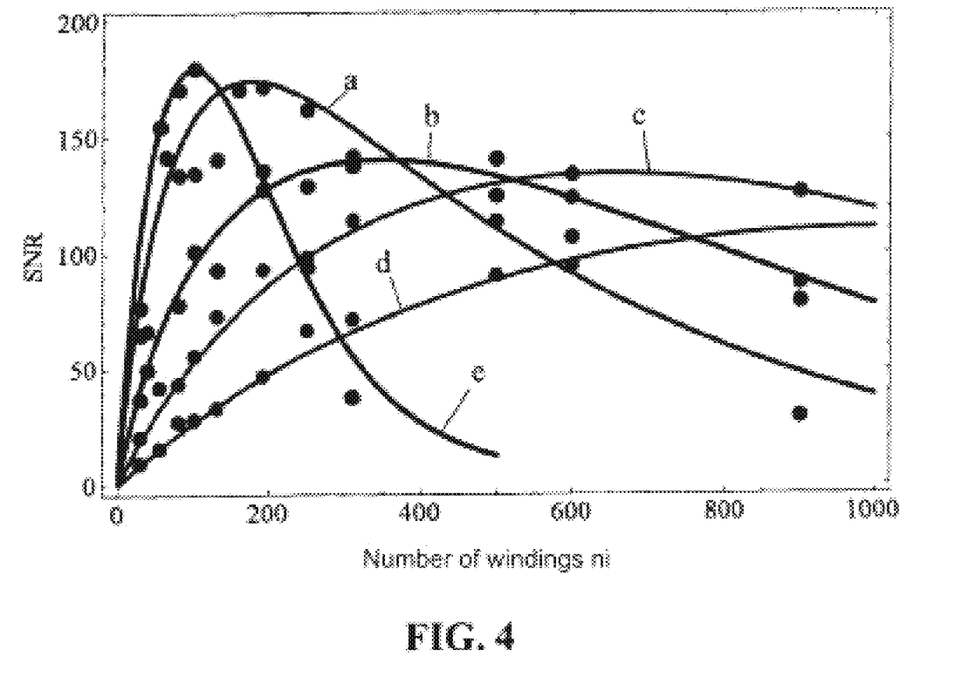
FIG. 4: Signal-to-noise ratio of benzene as a function of the number of windings nl of the pickup coil under the use of filter coils with ferrite cores

FIG. 4 shows the signal-to-noise ratio of benzene as a function of the number of windings $n_f$ of the pickup coil under use of filter coils with ferrite cores and after pre-polarization to $P_n=1.5 \times 10^{-6}$. Circles represent measured values and continuous lines correspond to the expected course. The frequencies f (and quality $Q_E$) amount to 500 kHz ($Q_E=218$, e), 166 kHz ($Q_E=280$, a), 83 kHz ($Q_E=369$, b), 41 kHz ($Q_E=380$, c) and 20 kHz ($Q_E=250$, d). The parameters of the filter coil are equal as in FIG. 3. FIG. 4 confirms based on experimental results, which were measured at the five different frequencies 500, 166, 83, 41 and 20 kHz, that at constant quality of the filter coil, the signal-to-noise ratio only depends very weakly from the frequency. When decreasing the frequency f, the measured maximum of the signal-to-noise ratio shifts towards higher values of $n_f$. From the maxima of the five curves the winding number $n_f^{max}$ can be read: $n_f^{max}=90, 140, 350, 750$ for f=500, 166, 83, and 41 kHz. The most important result of FIG. 4 is that the maximal signal-to-noise ratio decreases very weakly with the frequency. This means that measurements can be conducted with ferrite cores in the entire frequency range of some kHz (NMR in the earth's magnetic field) up to several MHz with high signal-to-noise ratio.

Figure 5:
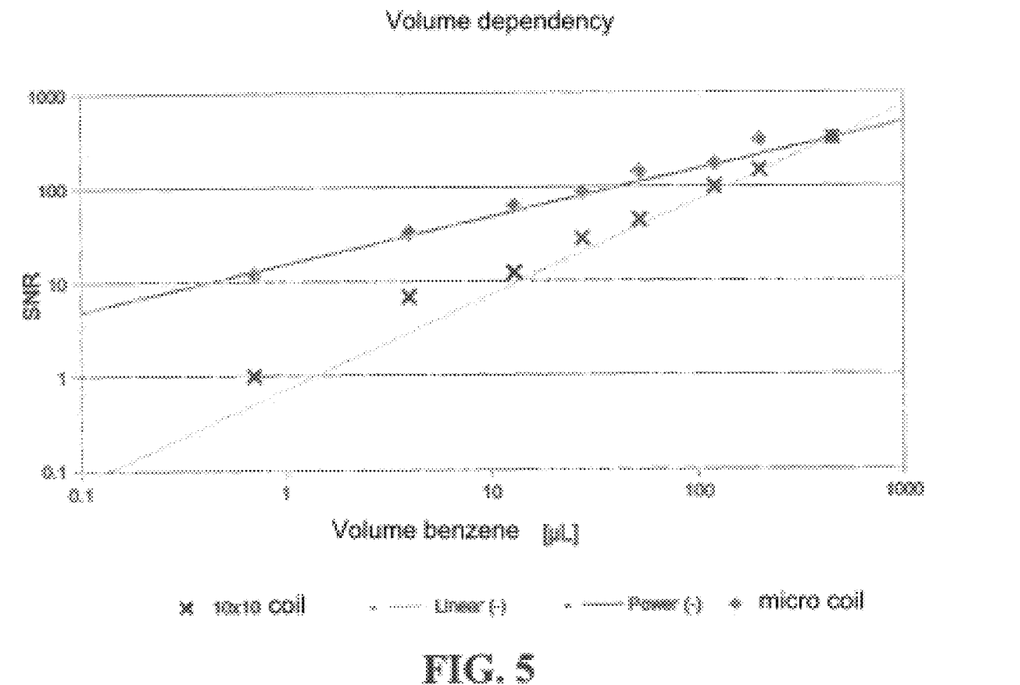
FIG. 5: Signal-to-noise ratio of $^1$H-NMR signals as a function of the volume Vs of a benzene sample In the following, a preferred embodiment is shown in FIG. 1.

FIG. 5 shows the signal-to-noise ration of $^1$H-NMR signals as a function of the volume $V_s$ of a benzene sample. It was measured after pre-polarization to $P_n=1.5 \times 10^{-6}$ at 500 kHz with a filter coil with ferrite core with $Q_E=218$. The crosses correspond to measurements, which were all conducted with the same input coil ($D_f=H_C=1$ cm) but with different sample volumes (0.7-500 µL). The rhombi correspond to measurements, at which input coil and sample are shrunk together by the same factor (1 mm<$D_f=H_C$<1 cm). The straight lines correspond to the expected run.

FIG. 5 illustrates based on two $^1$H-NMR experiments of benzene, how the signal-to-noise ratio is scaled with the volume of the sample. At the first experiment, the signal-to-noise ratio was measured at 500 kHz with a filter coil with ferrite core ($Q_E=218$) and with a fixed predefined pickup coil (parameter: $D_i=H_C=1$ cm, $n_f=160$, $d_{Cu}=0.12$ cm), but with different sample volumes $V_S$ (of 0.7 to 500 µL). At the second experiment, corresponding with the shrunk volume of the sample, also the volume respectively inner diameter $D_i$ and the height $H_C$ of the pickup coil were reduced, from $D_i=H_C=1$ cm to $D_i=H_C=0.1$ cm. The winding number $n_f=80$ was here kept constant. It can be seen in FIG. 5 that the measured signal-to-noise ratio scales in the first case with signal-to-noise ratio $\sim N_S \sim V_S$ and in the second case with signal-to-noise ratio $\sim N_S^{1/2} \sim V_S^{1/2}$ ($N_S$=number of the spins). This weak volume dependency in the second case is reducible to the increased sensitivity $\sim 1/D_i$ of the ever smaller becoming pickup coil. This result shows that with this method micro coil detected NMR spectroscopy at low frequencies and with µL size samples is possible. This is an important result in view of a miniaturization of mobile NMR spectroscopes. At frequencies below 10 MHz and for very small samples, the magnet, which generates the B-field, may be very small, portable, energy and cost efficiently manufactured. Energy efficiency means for example that a lithium-ion battery suffice to supply a small electro magnet with current. Cost efficiency manifests among others also during miniaturized permanent magnets, which need for their construction a comparatively far lower amount of magnetic material (rare earth).

At this point, it is also mentioned that the measured scaling signal-to-noise ratio $\sim V_S^{1/2}$ only applies for a winding number $n_f$ that is kept constant.

The invention claimed is:

1. A measuring device for detecting electromagnetic or magnetic alternating fields with an electromagnetic oscillating circuit, the device comprising
   a pickup coil (2),
   a tunable capacitance (4) and
   a filter coil (6),
   wherein at least one of the tunable capacitance (4), and filter coil (6), and the oscillating circuit have quality that is greater than 100 and
   wherein the quality of the filter coil (6) and the quality of the tunable capacitance (4) are at least two times greater than the quality of the pickup coil (2).

2. The device of claim 1, wherein the filter coil (6) of the oscillating circuit comprises a grounded center tapping (8).

3. The device of claim 1, wherein the filter coil (6) comprises two electric conductors that are twisted together, which are wound into the coil, wherein one respective end of each conductor is grounded.

4. The device of claim 1, wherein the filter coil (6) comprises a magnetic core (5), which in particular consists of ferrite.

5. The device of claim 1, wherein the filter coil (6) is shielded magnetically and electrically by a shielding (7).

6. The device of claim 5, wherein the shielding (7) is double-walled.

7. The device of claim 5 or 6, wherein the distance between the shielding (7) and the pickup coil (2) amounts to at least 1 cm.

8. The device of claim 1, further comprising a transfer line (3) between pickup coil (2) and capacitor as well as filter coil (6), which consists of two electric conductors that are wound around each other.

9. The device of claim 1, further comprising an excitation coil (12) for conducting EPR or NMR spectroscopy, which is separated from the pickup coil (2).

10. The device of claim 1, wherein the capacitance (4) is formed of a plurality of discrete capacitors that are connected in parallel.

11. The device of claim 1, wherein a differential amplifier (9), in particular an instrument amplifier, allows amplifying the voltage present at the filter coil (6).

12. The device of claim 11, wherein the differential amplifier is high resistance, specifically greater than $10^6$ ohm.

13. The device of claim 1, further comprising an outer shielding (10), in which the electric oscillating circuit comprising the pickup coil (2), the tunable capacitance (4) and the filter coil (6) are located and in particular moreover also an excitation coil (12), a transfer line (3) and/or an amplifier (9).

14. A method for detecting weak electromagnetic signals from a sample (1), the method comprising
providing a measuring device for detecting electromagnetic or magnetic alternating fields with an electromagnetic oscillating circuit, the measuring device including a pickup coil (2), a tunable capacitance (4), and a filter coil (6), wherein at least one of the tunable capacitance (4) and filter coil (6) and the oscillating circuit have high quality that is greater than 100 and wherein the quality of the filter coil (6) and the quality of the tunable capacitance (4) are at least two times greater than the quality of the pickup coil (2),
arranging the sample (1) within or on the surface of the pickup coil (2),
locating the sample (1) in a static magnetic field ($B_0$), and
exciting the sample (1) via a coil (12), which is separated from the pickup coil (2).

15. The method of claim 14, further comprising measuring a signal with a frequency of 1 kHz to 40 MHz.

* * * * *